United States Patent [19]

Grasselli et al.

[11] Patent Number: 4,778,930
[45] Date of Patent: Oct. 18, 1988

[54] PROCESS FOR THE OXIDATION OF OLEFINS USING CATALYSTS CONTANING ANTIMONY

[75] Inventors: Robert K. Grasselli, Chagrin Falls; Dev D. Surech, Warrensville Heights; Harley F. Hardman, Lyndhurst, all of Ohio

[73] Assignee: The Standard Oil Company, Cleveland, Ohio

[21] Appl. No.: 726,279

[22] Filed: Apr. 24, 1985

Related U.S. Application Data

[63] Continuation of Ser. No. 861,490, Dec. 19, 1977, abandoned, which is a continuation of Ser. No. 494,574, Aug. 5, 1974, abandoned.

[51] Int. Cl.[4] .................... C07C 45/00; C07C 47/28
[52] U.S. Cl. .................................. 568/477; 502/205
[58] Field of Search ..................... 562/546; 568/477; 502/205

[56] References Cited

U.S. PATENT DOCUMENTS

| | | | |
|---|---|---|---|
| 3,679,603 | 7/1972 | Garnish et al. | 252/432 |
| 3,761,424 | 9/1973 | Alzenau et al. | 252/437 |
| 3,825,502 | 7/1974 | Takemaka et al. | 252/456 |
| 4,001,317 | 1/1977 | Grasselli et al. | 260/533 N |
| 4,035,418 | 7/1977 | Okada et al. | 260/531 R |
| 4,075,127 | 2/1978 | Kadowaki et al. | 252/470 |
| 4,111,985 | 9/1978 | Okada et al. | 562/546 |
| 4,190,608 | 2/1980 | Grasselli et al. | 260/604 R |

FOREIGN PATENT DOCUMENTS

| | | |
|---|---|---|
| 950477 | 7/1971 | Canada . |
| 954880 | 7/1971 | Canada . |
| 956971 | 12/1971 | Canada . |
| 965437 | 1/1972 | Canada . |
| 1390114 | 6/1972 | United Kingdom . |
| 1298784 | 12/1972 | United Kingdom . |
| 1351646 | 5/1974 | United Kingdom . |
| 1456752 | 5/1974 | United Kingdom . |
| 1444659 | 5/1974 | United Kingdom . |

Primary Examiner—John F. Niebling
Attorney, Agent, or Firm—Larry W. Evans; David J. Untener; Michael F. Esposito

[57] ABSTRACT

The present invention is a process for the oxidation of olefins to unsaturated aldehydes and acids using a catalyst containing antimony, iron, bismuth, molybdenum plus at least one of nickel, cobalt, magnesium, zinc, cadmium or calcium within certain compositional limits. These catalysts may also contain certain elements that further enhance the desirability of the oxidation process.

7 Claims, No Drawings

PROCESS FOR THE OXIDATION OF OLEFINS USING CATALYSTS CONTANING ANTIMONY

This is a continuation of co-pending application Ser. No. 861,490 filed on Dec. 19, 1977, now abandoned, which is a continuation of Ser. No. 494,574 filed on Aug. 5, 1974, now abandoned.

SUMMARY OF THE INVENTION

The invention is in the process for the oxidation of propylene or isobutylene to produce the corresponding unsaturated aldehydes and acids by contacting the propylene or isobutylene with molecular oxygen in the presence of a catalyst at a temperature of about 200° to about 600° C., the improvement comprising using as the catalyst a catalyst of the formula $$Sb_aA_bD_cE_dFe_fBi_gMo_{12}O_x$$

wherein
A is an alkali metal, thallium or mixture thereof;
D is nickel, cobalt, magnesium, manganese, strontium, calcium, zinc, cadmium or mixture thereof;
E is phosphorus, arsenic, boron, tungsten or mixture thereof;
and wherein
a is greater than 0 but less than 5;
b and d are 0–4;
c is 0.1 to 20;
f and g are 0.1 to 10; and
X is the number of oxygens required to satisfy the valence requirements of the other elements present.

This oxidation reaction gives especially desirable results at atmospheric or superatmospheric pressure and especially desirable results in the oxidation of isobutylene.

The central aspect of the present invention is the particular catalyst employed. The catalysts may be any of the catalysts delimited by the formula described above. Preferred as far as the broad compositional structure of the catalyst is concerned are those catalysts that contain potassium, rubidium, cesium or mixture thereof and those catalysts that contain nickel, cobalt or mixture thereof.

The catalysts of the invention are prepared by techniques that are broadly known in the art. These techniques include the coprecipitation of soluble salts. More specific information on the preparation of the catalysts is given in the Specific Embodiments.

The catalysts of the invention may be used in the supported or unsupported form. Suitable support materials include silica, alumina, Alundum, titania, zirconia, silicon carbide and the like. The catalysts may also be used in various physical forms. The catalysts can be employed in a fixed-bed reactor or a fluid-bed reactor.

The process for oxidation of propylene or isobutylene is well known in the art. Broadly, a mixture of the olefin and molecular oxygen, optionally in the presence of steam or other diluent, is contacted with a catalyst at an elevated temperature of about 200°–600° C. for a contact time sufficient to convert the olefin to the corresponding unsaturated aldehyde and acid. Normally, the product from these reactions contains a very large portion of the aldehyde and a smaller by-product amount of the unsaturated acid. The contact time may vary widely from a few seconds to a number of seconds or more. The reaction can be conducted under atmospheric, superatmospheric or subatmospheric pressure with the use of a superatmospheric pressure normally being used on a commercial scale.

One special advantage of the catalysts of the invention is their ability to withstand the feed of large amounts of olefin over the catalyst in a given time. This is normally measured in terms of WWH which is the weight of olefin per weight of catalyst per hour. In other words, these catalysts can efficiently work on large amounts of olefin.

SPECIFIC EMBODIMENTS

Various catalysts of the invention were prepared as shown below. All catalysts contained 20% $SiO_2$.

EXAMPLE 1

$Sb_{0.5}K_{0.1}Ni_{2.5}Co_{4.5}Fe_3BiMo_{12}O_x$

A slurry of 63.56 g. $(NH_4)_6Mo_7O_{24}.4H_2O$, 61.79 g. of Nalco 34% silica sol and 2.19 g. $Sb_2O_3$ was prepared and combined with a solution of 36.36 g. $Fe(NO_3)_3.9H_2O$, 14.55 g. $Bi(NO_3)_3.5H_2O$, 39.29 g. $Co(NO_3)_2.6H_2O$, 21.80 g. $Ni(NO_3)_2.6H_2O$ and 3.03 g. of a 10% solution of $KNO_3$. The mixture was evaporated, dried, heat treated at 290° C. for three hours, 425° C. for three hours and 550° C. for 16 hours.

EXAMPLE 2

$SbK_{0.1}Cu_{0.1}Ni_{2.5}Co_{4.5}Fe_3BiMo_{12}O_x$

This catalyst was prepared in essentially the same way as shown in Example 1 but copper was added in the form of $Cu(NO_3)_2.3H_2O$.

EXAMPLES 3 AND 5

$Sb_{0.5}Cs_{0.5}Ni_{2.5}Co_{4.5}Fe_3BiMo_{12}O_x$

This catalyst was prepared in essentially the same manner as Example 1, except that $CsNO_3$ replaced the potassium compound.

EXAMPLES 4 AND 7

$Sb_{1.0}Cs_{0.5}S_{0.25}Ni_{2.5}Co_{4.5}Fe_3BiMo_{12}O_x$

The catalyst was prepared in the same manner as described above except that $Cs_2SO_4$ was employed to incorporate sulfur in the catalyst.

EXAMPLE 6

$Sb_{0.5}Cs_{0.2}Ni_{2.5}Co_{4.5}Fe_3BiMo_{12}O_x$

The catalyst was prepared in the same manner as shown in Example 1, except that $CsNO_3$ was employed rather than the potassium.

In a fixed-bed reactor constructed of a 0.75 cm. inside diameter stainless steel tube was placed 5 cc. of each catalyst prepared above. The catalysts were tested at a temperature of 371° C. using a feed of isobutylene/air/steam of 1/10/4 and an apparent contact time of 3.7±0.4 seconds.

The results of these experiments are given in the Table.

The results are stated as follows:

$$\% \text{ yield per pass} = \frac{\text{moles of product} \times 100}{\text{moles of isobutylene fed}}$$

$$\% \text{ conversion} = \frac{\text{moles of isobutylene reacted} \times 100}{\text{moles of isobutylene fed}}$$

$$\% \text{ selectivity} = \frac{\text{moles of product formed} \times 100}{\text{moles of isobutylene reacted}}$$

In the Table MA is methacrolein and MAA is methacrylic acid.

TABLE

Oxidation of Isobutylene to Methacrolein and Methacrylic Acid Using a Catalyst of $YNi_{2.5}Co_{4.5}Fe_3BiMo_{12}O_x$

| Example | Catalyst Y= | Yield Per Pass MA | Yield Per Pass MMA | Yield Per Pass Total | Conversion | Selectivity |
|---|---|---|---|---|---|---|
| 1 | $Sb_{0.5}K_{0.1}$ | 60.8 | 4.9 | 65.7 | 100.0 | 65.7 |
| 2 | $Sb_{0.5}K_{0.1}Cu_{0.1}$ | 66.1 | 1.4 | 67.5 | 100.0 | 67.5 |
| 3 | $Sb_{0.5}Cs_{0.5}$ | 80.3 | 3.3 | 83.6 | 99.4 | 84.2 |
| 4 | $Sb_{1.0}Cs_{0.5}S_{0.25}$ | 74.1 | 1.0 | 75.1 | 82.1 | 91.4 |
| 5[a] | $Sb_{0.5}Cs_{0.5}$ | 61.1 | 8.5 | 69.6 | 98.8 | 70.5 |
| 6[a] | $Sb_{0.5}Cs_{0.2}$ | 66.1 | 5.3 | 71.4 | 100.0 | 71.4 |
| 7[b] | $Sb_{1.0}Cs_{0.5}S_{0.25}$ | 77.2 | 1.6 | 78.8 | 92.8 | 85.0 |

[a] pressure 12 p.s.i.g.
[b] pressure 9.7 p.s.i.g.

EXAMPLE 8

Preparation of acrolein and acrylic acid

In the same manner as described in the examples above, a catalyst of $Sb_{0.5}K_{0.1}Ni_{2.5}Co_{4.5}Fe_3BiMo_{12}O_x$ was prepared and used in the oxidation of propylene. The catalyst was placed in a 5 cc. reaction zone of a reactor constructed of a stainless steel tube. The temperature of the reaction zone was maintained at 380° C. and the apparent contact time was three seconds. A feed of propylene/air/steam of 1/11/4 was employed. Of the propylene fed, 96.8% was converted with a selectivity to acrolein and acrylic acid of 94.9%. The yield per pass of acrolein was 78.1%, the yield per pass of acrylic acid was 13.8% and the total yield per pass to acrolein and acrylic acid was 91.9%.

We claim:

1. A process for the oxidation of isobutylene to produce the corresponding unsaturated aldehyde by contacting isobutylene with molecular oxygen in the presence of a catalyst having the composition:

$$L_aFe_bBi_cB_dSb_eJ_gMo_hO_i$$

in which

L is a mixture of cobalt and nickel,

J represents at least one element selected from the group consisting of potassium, rubidium and cesium, a, b, c, d, e, g, h, and i represent the numbers of L, iron, bismuth, boron, antimony, J, molybdenum and oxygen atoms, respectively, with the proviso that the elements are present in a ratio so that when h is 12, a is 0.1 to 20, b is 0.1 to 10, c is 0.1 to 10, d is greater than zero and less than or equal to 4, e is greater than zero but less than 5, g is greater than zero and less than or equal to 4 and i is the number of oxygens required to satisfy the valence requirements of the other elements present.

2. A process for the oxidation of isobutylene to produce the corresponding unsaturated aldehyde by contacting isobutylene with molecular oxygen in the presence of a catalyst having the composition:

$$L_aFe_bBi_cB_dSb_eJ_gMo_hO_i$$

in which

L is cobalt or a mixture of cobalt and nickel,

J represents at least one element selected from the group consisting of potassium, rubidium and cesium, a, b, c, d, e, g, h, and i represent the numbers of L, iron, bismuth, boron, antimony, J, molybdenum and oxygen atoms, respectively, with the proviso that the elements are present in a ratio so that when h is 12, a is 0.1 to 20, b is 0.1 to 10, c is 0.1 to 10, d is greater than zero and less than or equal to 4, e is greater than zero but less than 5, g is greater than zero and less than or equal to 4 and i is the number of oxygens required to satisfy the valence requirements of the other elements present.

3. The process of claim 2 wherein h is 12, a is 3 to 12, b is 0.5 to 3, c is 0.5 to 4, d is 0.5 to 3, e is 0.05 to 1, f is 0 to 3, g is 0.01 to 0.5 and i is 42 to 77.

4. The process of claim 2 wherein the reaction is carried out in the presence of steam.

5. The process of claim 2 wherein the reactant is isobutylene.

6. An oxidation catalyst having the composition $$L_aFe_bBi_cB_dSb_eJ_gMo_nO_i$$

in which

L is cobalt, or a mixture of cobalt and nickel,

J represents at least one element selected from the group consisting of potassium, rubidium and cesium, a, b, c, d, e, g, h, and i represent the numbers of L, iron, bismuth, boron, antimony, J, molybdenum and oxygen atoms, respectively, with the proviso that the elements are present in a ratio so that when h is 12, a is 0.1 to 20, b is 0.1 to 10, c is 0.1 to 10, d is greater than zero and less than or equal to 4, e is greater than zero but less than 5, g is greater than zero and less than or equal to 4 and i is the number of oxygens required to satisfy the valence requirements of the other elements present.

7. The oxidation catalyst of claim 6 wherein the ratio is such that when h is 12, a is 3 to 12, b is 0.5 to 5, c is 0.5 to 4, d is 0.5 to 3, e is 0.05 to 1, f is 0 to 3, g is 0.01 to 0.05 and i is 42 to 77.

* * * * *